US011116946B2

(12) United States Patent
Ruel

(10) Patent No.: US 11,116,946 B2
(45) Date of Patent: Sep. 14, 2021

(54) URINARY CATHETER DEVICE

(71) Applicant: Steven Ruel, St-Isidore deClifton (CA)

(72) Inventor: Steven Ruel, St-Isidore deClifton (CA)

( * ) Notice: Subject to any disclaimer, the term of this patent is extended or adjusted under 35 U.S.C. 154(b) by 476 days.

(21) Appl. No.: 16/014,357

(22) Filed: Jun. 21, 2018

(65) Prior Publication Data

US 2019/0388659 A1    Dec. 26, 2019

(51) Int. Cl.
*A61M 25/10* (2013.01)
*A61M 25/00* (2006.01)

(52) U.S. Cl.
CPC .... *A61M 25/10185* (2013.11); *A61M 25/007* (2013.01); *A61M 2210/1085* (2013.01); *A61M 2210/1089* (2013.01)

(58) Field of Classification Search
CPC .... A61M 25/10185; A61M 2210/1089; A61M 25/007; A61M 25/0017; A61M 2025/0019; A61M 2210/1085; A61M 25/0074; A61M 2025/0188; A61M 25/10; A61M 2025/0078; A61M 25/0023; Y10S 128/25
See application file for complete search history.

(56) References Cited

U.S. PATENT DOCUMENTS

| | | | | |
|---|---|---|---|---|
| 2,919,697 A | * | 1/1960 | Kyong | A61M 25/1002 604/102.02 |
| 3,331,371 A | | 7/1967 | Rocchi | |
| 4,227,533 A | | 10/1980 | Godfrey | |
| 4,228,802 A | | 10/1980 | Trott | |
| 4,249,536 A | * | 2/1981 | Vega | A61M 25/0068 604/103 |
| 6,093,191 A | | 7/2000 | Porter | |
| 6,167,886 B1 | * | 1/2001 | Engel | A61F 2/0027 128/885 |
| 8,038,644 B2 | | 10/2011 | Glickman | |

* cited by examiner

*Primary Examiner* — Catharine L Anderson
*Assistant Examiner* — Arjuna P Chatrathai

(57) ABSTRACT

A urinary catheter device having a means for unblocking the catheter includes a tube, which has a distal end that is closed. The tube is resilient and is configured to insert through a urethra of an animal to position the distal end in a bladder. A hole is positioned through a wall of the tube proximate to the distal end and is configured to drain urine from the bladder through a proximal end of the tube, which is open. A channel extends through the wall from a first valve that is coupled to the tube to a chamber that is positioned in the wall proximate to the hole. Introduction of a fluid via the first valve into the chamber expands the chamber and increases a circumference of the hole so that debris that is impeding a flow of the urine through the tube enters and passes through the tube.

9 Claims, 6 Drawing Sheets

US 11,116,946 B2

URINARY CATHETER DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to catheter devices and more particularly pertains to a new catheter device having a means for unblocking the catheter.

BRIEF SUMMARY OF THE INVENTION

An embodiment of the disclosure meets the needs presented above by generally comprising a tube, which has a distal end that is closed. The tube is resilient and is configured to insert through a urethra of an animal to position the distal end in a bladder. A hole is positioned through a wall of the tube proximate to the distal end and is configured to drain urine from the bladder through a proximal end of the tube, which is open. A channel extends through the wall from a first valve that is coupled to the tube to a chamber that is positioned in the wall proximate to the hole. Introduction of a fluid via the first valve into the chamber expands the chamber and increases a circumference of the hole so that debris that is impeding a flow of the urine through the tube enters and passes through the tube.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
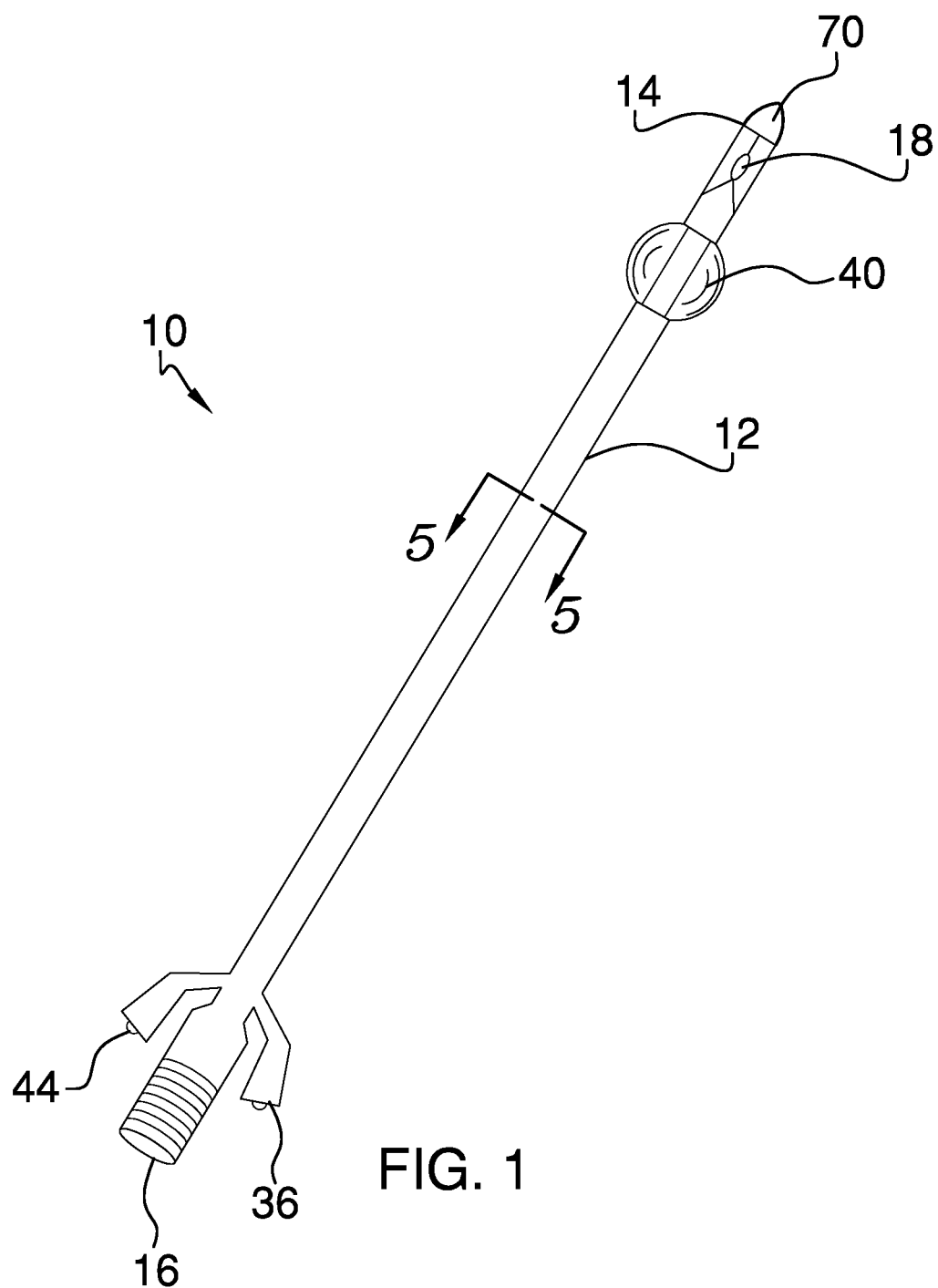
FIG. 1 is an isometric perspective view of a urinary catheter device according to an embodiment of the disclosure.

With reference now to the drawings, and in particular to FIGS. 1 through 7 thereof, a new catheter device embodying the principles and concepts of an embodiment of the disclosure and generally designated by the reference numeral 10 will be described.

As best illustrated in FIGS. 1 through 7, the urinary catheter device 10 generally comprises a tube 12 that has a distal end 14 and a proximal end 16. The distal end 14 is closed. The proximal end 16 is open. The tube 12 is resilient and is configured to insert through a urethra of an animal to position the distal end 14 in a bladder of the animal.

A hole 18 is positioned through a wall 20 of the tube 12 proximate to the distal end 14. The hole 18 is configured to allow entry of urine into the tube 12 so that the urine flows toward the proximal end 16 to drain the bladder.

Figure 6:
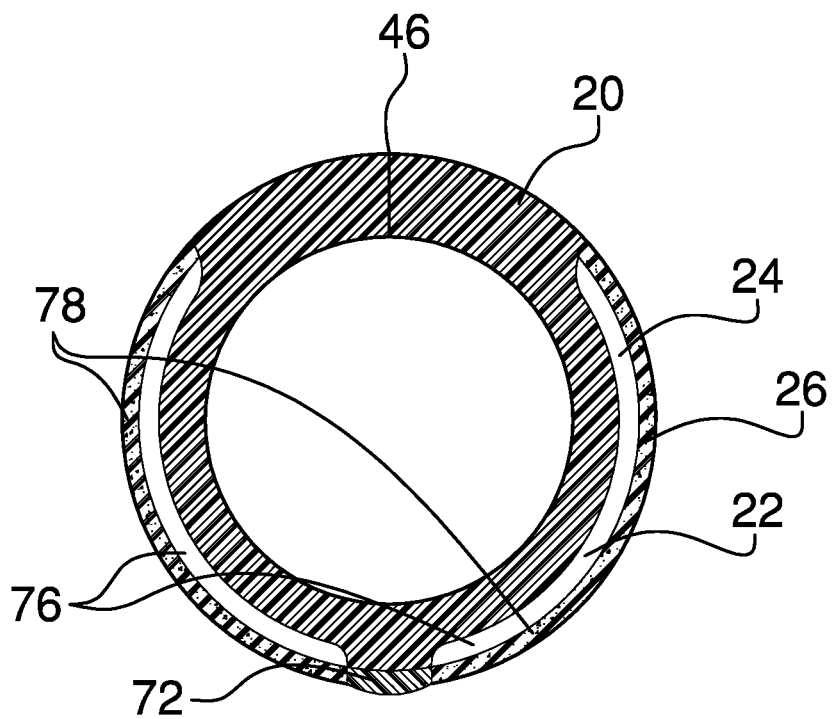
FIG. 6 is a cross-sectional view of an embodiment of the disclosure.

A chamber 22 is positioned in the wall 20 of the tube 12 proximate to the hole 18, as shown in FIG. 6. The chamber 22 is defined by a recess 24 and a panel 26. The recess 24 extends into the wall 20 from an outer circumference 28 of the tube 12. The panel 26 is coupled to a perimeter 30 of the recess 24 and extends from the wall 20 to cover the recess 24. The panel 26 comprises silicone so that the chamber 22 comprises a compliant balloon 32.

Figure 5:
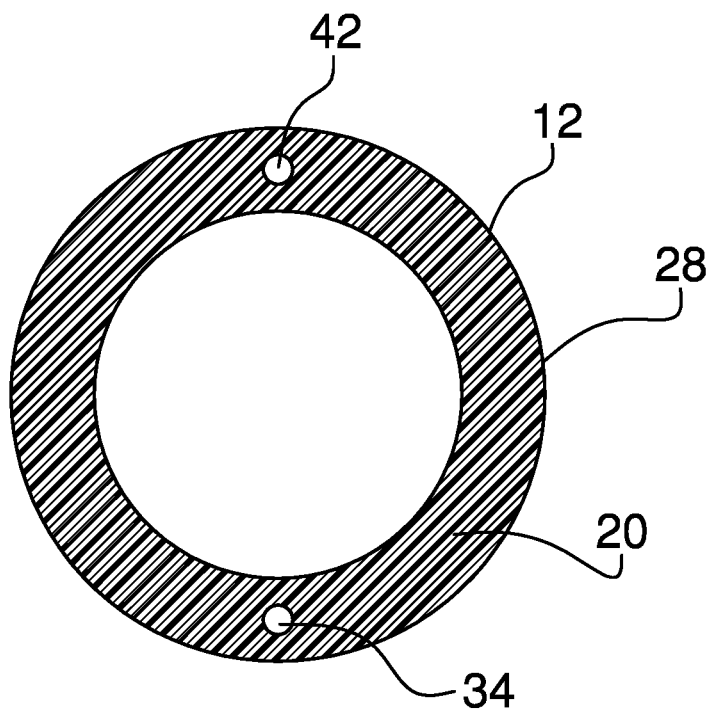
FIG. 5 is a cross-sectional view of an embodiment of the disclosure.

A channel 34 extends from the chamber 22 through the wall 20, as shown in FIG. 5, to a first valve 36 that is coupled to the tube 12 proximate to the proximal end 16, as shown in FIG. 1. The first valve 36 is configured to introduce a fluid through the channel 34 into the chamber 22 to expand the chamber 22 to selectively increase a circumference 38 of the hole 18 so that debris that impedes a flow of the urine through the tube 12 enters and passes through the tube 12.

A retention balloon 40 is coupled to the tube 12 proximate to the chamber 22 so that the retention balloon 40 is positioned between the chamber 22 and the proximal end 16 of the tube 12, as shown in FIG. 1. A balloon channel 42 extends through the wall 20, as shown in FIG. 5, to a second valve 44 that is coupled to the tube 12 proximate to the proximal end 16, as shown in FIG. 1. The second valve 44 is configured to introduce a fluid through the balloon channel 42 into the retention balloon 40 to expand the retention balloon 40 within the bladder to fixedly position the tube 12.

Figure 2:
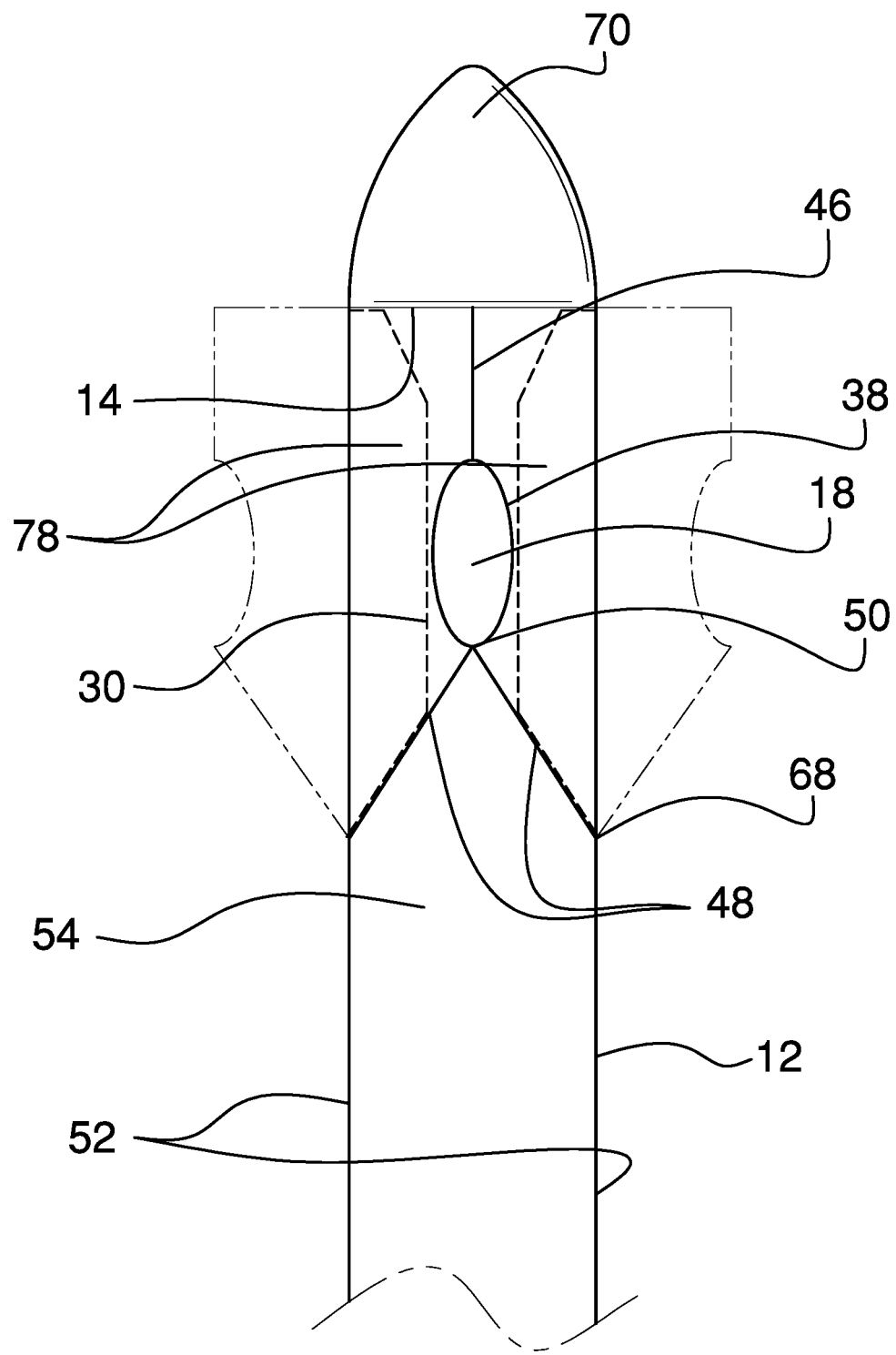
FIG. 2 is a top view of an embodiment of the disclosure.

A first slit 46 is positioned through the wall 20. The first slit 46 extends from the hole 18 to proximate to the distal end 14 of the tube 12, as shown in FIG. 2. The first slit 46 is configured to separate concurrently with expansion of the chamber 22 to increase the circumference 38 of the hole 18 so that the debris that impedes the flow of the urine through the tube 12 enters and passes through the tube 12. The first slit 46 is configured to substantially and sealably close upon draining of the fluid from the chamber 22.

A pair of second slits 48 is positioned through the wall 20, as shown in FIG. 2. Each second slit 48 has a first endpoint 50 that is opposingly positioned on the hole 18 relative to the first slit 46. Each second slit 48 extends transversely to a respective opposing side 52 of the tube 12 so that the pair of second slits 48 is substantially V-shaped when viewed from a top 54 of the tube 12. The second slits 48 are configured to separate concurrently with expansion of the chamber 22 to increase the circumference 38 of the hole 18 so that the debris that impedes the flow of the urine through the tube 12 enters and passes through the tube 12. The second slits 48 are configured to substantially and sealably close upon draining of the fluid from the chamber 22.

Figure 3:
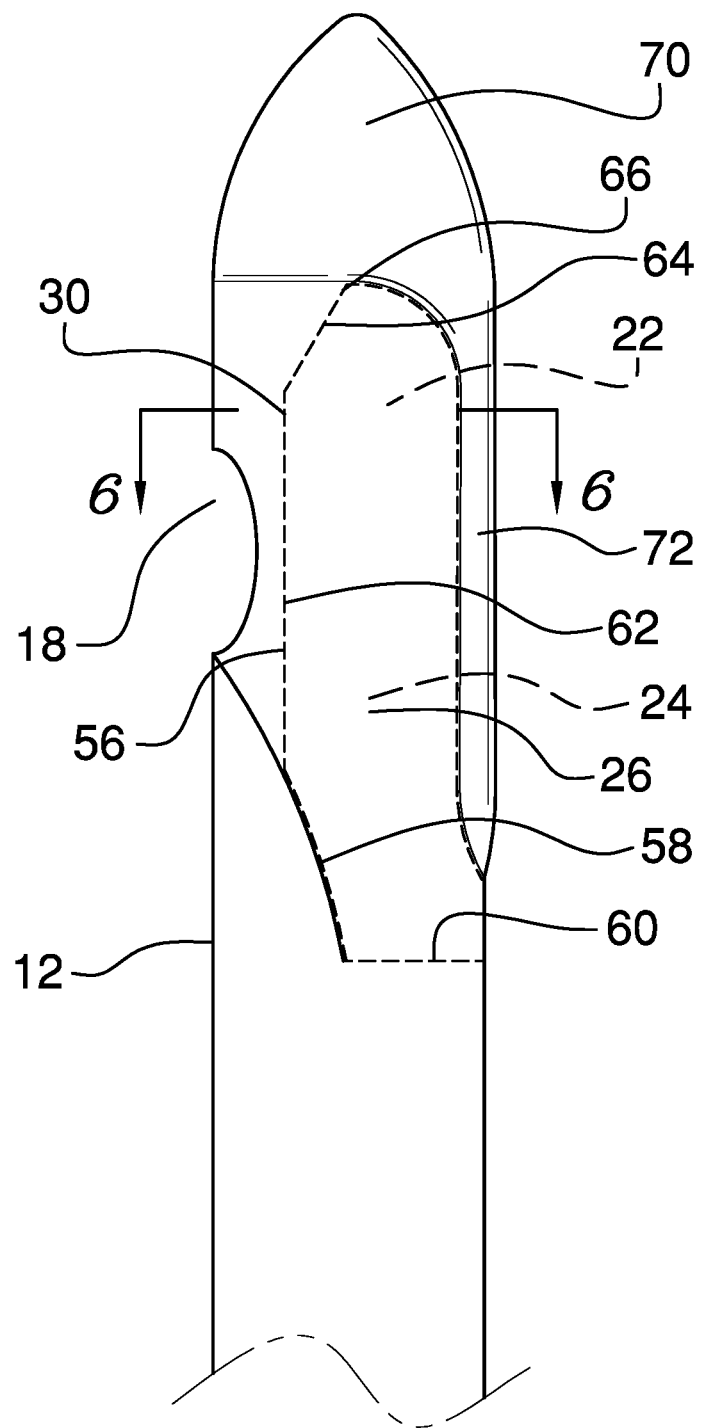
FIG. 3 is a side view of an embodiment of the disclosure.
Figure 4:
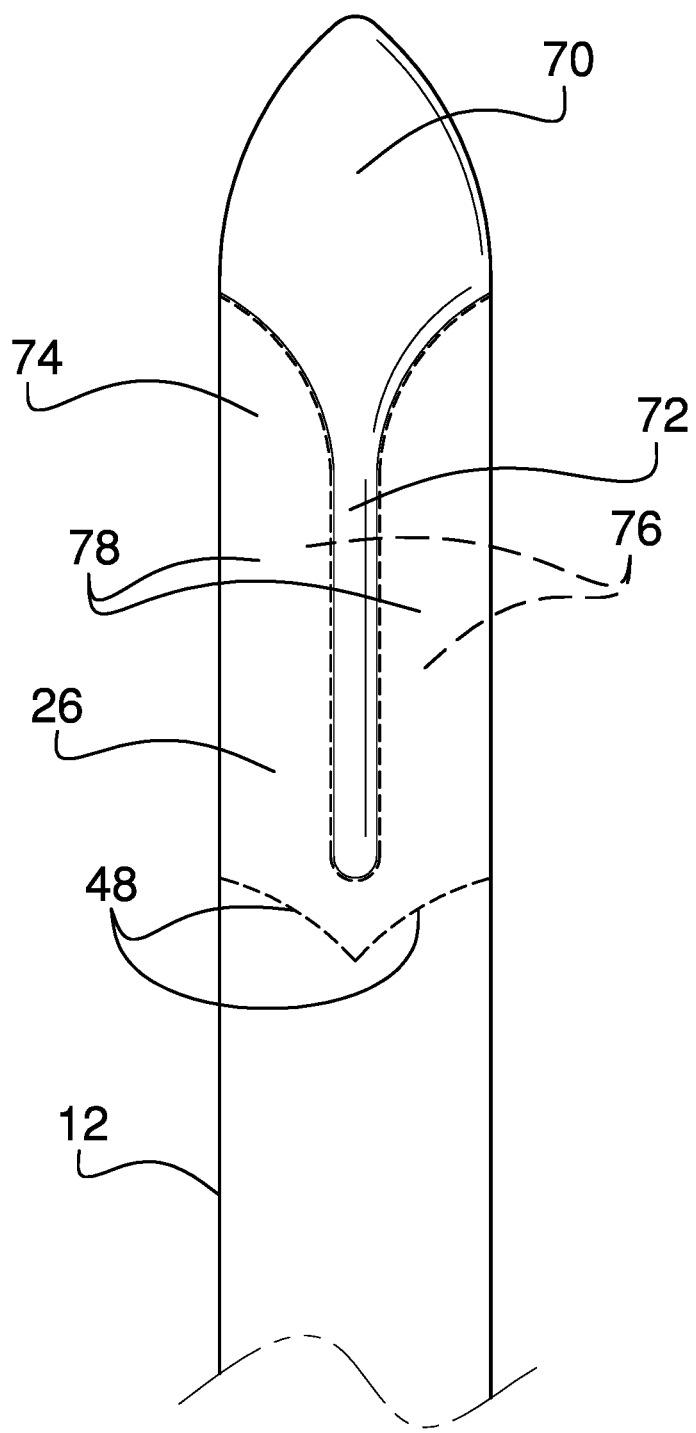
FIG. 4 is a bottom view of an embodiment of the disclosure.

The recess 24 comprises a pair of upper edges 56, a pair of transition edges 58, and a proximal edge 60, as shown in FIG. 3. The upper edges 56 bracket the hole 18. Each upper edge 56 extends from proximate to a respective second slit 48 to proximate to the distal end 14 of the tube 12. Each upper edge 56 comprises a first segment 62 and a second segment 64. The first segment 62 extends from the respective second slit 48 past the hole 18. The second segment 64 extends transversely from the first segment 62 to proximate to the distal end 14 of the tube 12 so that a terminus 66 of the second segment 64 is in substantial alignment with a second endpoint 68 of the respective second slit 48.

Each transition edge 58 extends along the respective second slit 48 to proximate to the second endpoint 68 of the respective second slit 48. The proximal edge 60 extends between the pair of transition edges 58. The channel 34 meets the chamber 22 at the proximal edge 60 so that the chamber 22 is in fluidic communication with the first valve 36.

A tip 70 is coupled to and extends from the distal end 14 of the tube 12, as shown in FIG. 3. The tip 70 is configured to facilitate insertion of the tube 12 through the urethra of the animal to position the hole 18 in the bladder of the animal. The tip 70 is substantially conically shaped.

A slat 72 is coupled to and extends from the tip 70 along a bottom 74 of the tube 12 to proximate to the proximal edge 60 of the recess 24, as shown in FIG. 3. The slat 72 is coupled to the wall 20 so that the slat 72 defines a pair of compartments 76 within the chamber 22 and a pair of sections 78 of the panel 26, as shown in FIG. 6. The compartments 76 are in fluidic communication. The slat 72 serves to provide structure to the tube 12 proximate to the distal end 14 to facilitate insertion of the tube 12 through the urethra.

Figure 7:
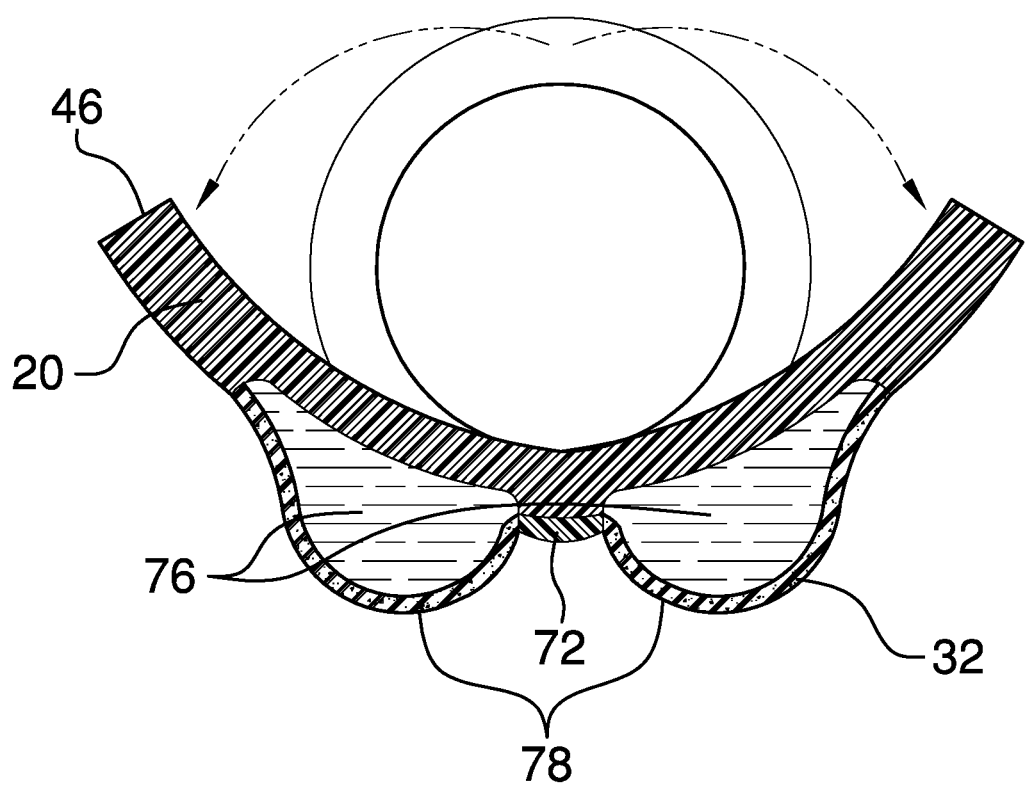
FIG. 7 is a cross-sectional view of an embodiment of the disclosure.

Introduction of the fluid through the channel 34 into the compartments 76 induces an expansion of each compartment 76, as shown in FIG. 7, so that an associated section 78 of the panel 26 pulls on the wall 20 to separate the first slit 46 and the second slits 48 to increase the circumference 38 of the hole 18 so that the debris that impedes the flow of the urine through the tube 12 enters and passes through the tube 12. The slat 72 is tapered and arcuate distal from the tip 70 to facilitate extraction of the tube 12 from the urethra.

In use, the tube 12 is inserted through the urethra to position the hole 18 in the bladder. The second valve 44 then is used to introduce the fluid into the retention balloon 40 to fixedly position the tube 12. If debris should block or partially block the hole 18, the fluid can be introduced into the chamber 22 to increase the circumference 38 of the hole 18, allowing the debris to pass through the tube 12.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A urinary catheter device comprising:
   a tube having a distal end and a proximal end, the distal end being closed, the proximal end being open, the tube being resilient wherein the tube is configured for inserting through a urethra of an animal positioning the distal end in a bladder of the animal;
   a hole positioned through a wall of the tube proximate to the distal end wherein the hole is configured for entry of urine into the tube such that the urine flows toward the proximal end for draining the bladder;
   a chamber positioned in the wall of the tube proximate to the hole, the chamber being defined by a recess and a panel, the recess extending into the wall from an outer circumference of the tube, the panel being coupled to a perimeter of the recess and extending from the wall to cover the recess, the panel comprising silicone such that the chamber comprises a compliant balloon, the recess comprising:
      a pair of upper edges, each upper edge extending from adjacent to a respective second slit towards the distal end of the tube;
      a pair of transition edges, each transition edge extending along the respective second slit towards a second endpoint of the respective second slit; and
      a proximal edge extending between the pair of transition edges;
   a channel extending from the chamber through the wall to a first valve coupled to the tube proximate to the proximal end wherein the first valve is configured for introducing a fluid through the channel into the chamber for expanding the chamber for selectively increasing a circumference of the hole such that debris impeding a flow of the urine through the tube enters and passes through the tube, the channel meeting the chamber at the proximal edge such that the chamber is in fluidic communication with the first valve; and a first slit positioned through the wall, the first slit extending from the hole towards the distal end of the tube wherein the first slit is configured for separating concurrent with expansion of the chamber for increasing the circumference of the hole such that the debris impeding the flow of the urine through the tube enters and passes through the tube, wherein the first slit is configured for closing upon draining of the fluid from the chamber.

2. The device of claim 1, further comprising:
a retention balloon coupled to the tube proximate to the chamber such that the retention balloon is positioned between the chamber and the proximal end of the tube; and
a balloon channel extending through the wall to a second valve coupled to the tube proximate to the proximal end wherein the second valve is configured for introducing a fluid through the balloon channel into the retention balloon for expanding the retention balloon within the bladder for fixedly positioning the tube.

3. The device of claim 1, further including a pair of second slits positioned through the wall, each second slit having a first endpoint opposingly positioned on the hole relative to the first slit, each second slit extending transversely to a respective opposing side of the tube such that the pair of second slits is substantially V-shaped when viewed from a top of the tube wherein the second slits are configured for separating concurrent with expansion of the chamber for increasing the circumference of the hole such that the debris impeding the flow of the urine through the tube enters and passes through the tube, wherein the second slits are configured for closing upon draining of the fluid from the chamber.

4. The device of claim 1, further including each upper edge comprising a first segment and a second segment, the first segment extending from the respective second slit past the hole, the second segment extending transversely from the first segment towards the distal end of the tube such that a terminus of the second segment is in substantial alignment with the second endpoint of the respective second slit.

5. The device of claim 1, further including a tip coupled to and extending from the distal end of the tube wherein the tip is configured for facilitating insertion of the tube through the urethra of the animal positioning the hole in the bladder of the animal.

6. A urinary catheter device comprising:
a tube having a distal end and a proximal end, the distal end being closed, the proximal end being open, the tube being resilient wherein the tube is configured for inserting through a urethra of an animal positioning the distal end in a bladder of the animal;
a hole positioned through a wall of the tube proximate to the distal end wherein the hole is configured for entry of urine into the tube such that the urine flows toward the proximal end for draining the bladder;
a chamber positioned in the wall of the tube proximate to the hole;
a channel extending from the chamber through the wall to a first valve coupled to the tube proximate to the proximal end wherein the first valve is configured for introducing a fluid through the channel into the chamber for expanding the chamber for selectively increasing a circumference of the hole such that debris impeding a flow of the urine through the tube enters and passes through the tube; and
a slat coupled to and extending from the tip along a bottom of the tube to proximate to the proximal edge of the recess, the slat being coupled to the wall such that the slat defines a pair of compartments within the chamber and a pair of sections of the panel, the compartments being in fluidic communication wherein introduction of the fluid through the channel into the compartments induces an expansion of each compartment such that an associated section of the panel pulls on the wall for separating the first slit and the second slits for increasing the circumference of the hole such that the debris impeding the flow of the urine through the tube enters and passes through the tube.

7. The device of claim 6, further including the slat being tapered and arcuate distal from the tip for facilitating extraction of the tube from the urethra.

8. The device of claim 5, further including the tip being substantially conically shaped.

9. A urinary catheter device comprising:
a tube having a distal end and a proximal end, the distal end being closed, the proximal end being open, the tube being resilient wherein the tube is configured for inserting through a urethra of an animal positioning the distal end in a bladder of the animal;
a hole positioned through a wall of the tube proximate to the distal end wherein the hole is configured for entry of urine into the tube such that the urine flows toward the proximal end for draining the bladder;
a chamber positioned in the wall of the tube proximate to the hole, the chamber being defined by a recess and a panel, the recess extending into the wall from an outer circumference of the tube, the panel being coupled to a perimeter of the recess and extending from the wall to cover the recess, the panel comprising silicone such that the chamber comprises a compliant balloon;
a channel extending from the chamber through the wall to a first valve coupled to the tube proximate to the proximal end wherein the first valve is configured for introducing a fluid through the channel into the chamber for expanding the chamber for selectively increasing a circumference of the hole such that debris impeding a flow of the urine through the tube enters and passes through the tube;
a retention balloon coupled to the tube proximate to the chamber such that the retention balloon is positioned between the chamber and the proximal end of the tube;
a balloon channel extending through the wall to a second valve coupled to the tube proximate to the proximal end wherein the second valve is configured for introducing a fluid through the balloon channel into the retention balloon for expanding the retention balloon within the bladder for fixedly positioning the tube;
a first slit positioned through the wall, the first slit extending from the hole towards the distal end of the tube wherein the first slit is configured for separating concurrent with expansion of the chamber for increasing the circumference of the hole such that the debris impeding the flow of the urine through the tube enters and passes through the tube, wherein the first slit is configured for closing upon draining of the fluid from the chamber;
a pair of second slits positioned through the wall, each second slit having a first endpoint opposingly positioned on the hole relative to the first slit, each second slit extending transversely to a respective opposing side of the tube such that the pair of second slits is substantially V-shaped when viewed from a top of the tube wherein the second slits are configured for separating concurrent with expansion of the chamber for increasing the circumference of the hole such that the debris impeding the flow of the urine through the tube enters and passes through the tube, wherein the second slits are configured for closing upon draining of the fluid from the chamber, the recess comprising:
a pair of upper edges, each upper edge extending from proximate to a respective second slit towards the distal end of the tube, each upper edge comprising a first segment and a second segment, the first segment extending from the respective second slit past the hole, the second segment extending transversely from the first segment towards the distal end of the tube such that a terminus of the second segment is in substantial alignment with a second endpoint of the respective second slit,
a pair of transition edges, each transition edge extending along the respective second slit towards the second endpoint of the second slit, and
a proximal edge extending between the pair of transition edges, the channel meeting the chamber at the proximal edge such that the chamber is in fluidic communication with the first valve;
a tip coupled to and extending from the distal end of the tube wherein the tip is configured for facilitating insertion of the tube through the urethra of the animal positioning the hole in the bladder of the animal, the tip being substantially conically shaped; and
a slat coupled to and extending from the tip along a bottom of the tube to proximate to the proximal edge of the recess, the slat being coupled to the wall such that the slat defines a pair of compartments within the chamber and a pair of sections of the panel, the compartments being in fluidic communication wherein introduction of the fluid through the channel into the compartments induces an expansion of each compartment such that an associated section of the panel pulls on the wall for separating the first slit and the second slits for increasing the circumference of the hole such that the debris impeding the flow of the urine through the tube enters and passes through the tube, the slat being tapered and arcuate distal from the tip for facilitating extraction of the tube from the urethra.

* * * * *